United States Patent [19]  
Ozutsumi et al.

[11] 3,967,835  
[45] July 6, 1976

[54] PRESSURE-SENSITIVE COPYING MATERIAL

[75] Inventors: Minoru Ozutsumi; Yoshihide Miyazawa; Masahiko Yamaguchi, all of Tokyo; Akio Watanabe; Keiso Saeki, both of Fujimiya, all of Japan

[73] Assignees: Hodogaya Chemical Co., Ltd., Tokyo; Fuji Photo Film Co., Ltd., Minami-ashigara, both of Japan

[22] Filed: July 8, 1975

[21] Appl. No.: 594,174

[30] Foreign Application Priority Data  
July 8, 1974 Japan.............................. 49-77433

[52] U.S. Cl............................ 282/27.5; 260/244 R; 260/340.3; 427/151; 427/152; 428/323; 428/411; 428/914
[51] Int. Cl.².......................................... B41M 5/16
[58] Field of Search............ 427/146, 145, 150–152, 427/261; 428/307, 323, 411, 537, 914; 282/27.5; 260/244 R, 340.3

[56] References Cited  
UNITED STATES PATENTS

| 3,006,917 | 10/1961 | Seegar............................. 260/244 R |
| 3,244,549 | 4/1966 | Farnham et al..................... 282/27.5 |
| 3,684,549 | 8/1972 | Shank............................... 428/476 |

Primary Examiner—Thomas J. Herbert, Jr.  
Assistant Examiner—Bruce H. Hess  
Attorney, Agent, or Firm—Sughrue, Rothwell, Mion, Zinn & Macpeak

[57] ABSTRACT

A pressure-sensitive copying material comprising a support having thereon a microencapsulated color former capable of forming a distinct color when reacted with an electron-accepting solid, the microencapsulated color former comprising at least one benzoxazine derivative represented by the formula (Ia)

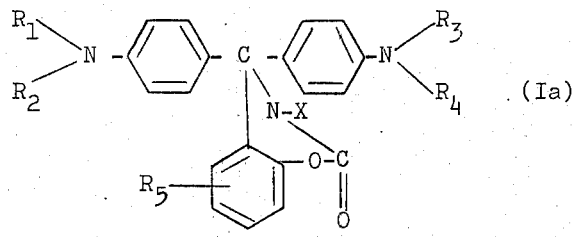

, a benzodioxane derivative represented by the formula (Ib)

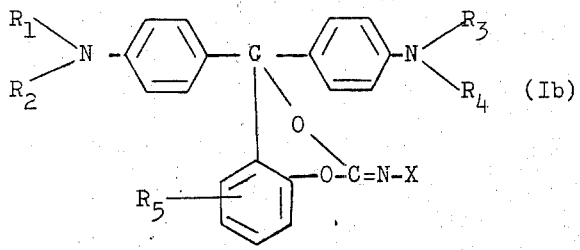

and a mixture thereof, wherein $R_1$, $R_2$, $R_3$, $R_4$, $R_5$ and X are as defined hereinafter.

8 Claims, No Drawings

PRESSURE-SENSITIVE COPYING MATERIAL

BACKGROUND OF THE INVENTION

1. Field of the Invention

This invention relates to a pressure-sensitive copying material.

2. Description of the Prior Art

In general, a pressure-sensitive copying member, comprises the combination of an upper sheet having coated on the back surface thereof minute microcapsules having dissolved therein an electron-donating substantially colorless organic compound capable of undergoing a color reaction, i.e., color former, and a lower sheet having coated on the surface thereof an electron-accepting material, i.e., a color developer. When these two coated surfaces are brought into contact with each other and a localized pressure is applied to the assembly by handwriting or typewriting, microcapsules located at the pressure-applied area are ruptured and the organic color former contained in the organic solvent comes into contact with the color developer to form color.

SUMMARY OF THE INVENTION

As a result of detailed investigations on the color former for pressure-sensitive copying members, it has now been found that a pressure-sensitive copying material capable of forming a purple to green color can be obtained by using as a color former a novel benzoxazine derivative represented by the formula (Ia)

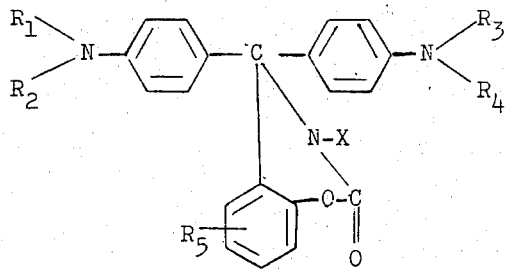

(Ia)

a novel benzodioxane derivative represented by the formula (Ib)

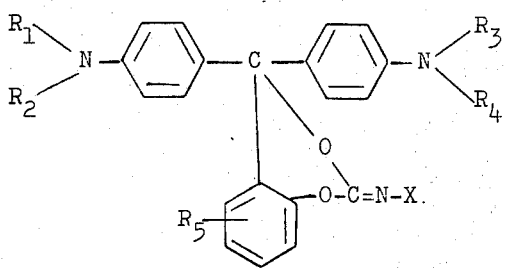

(Ib), or a mixture thereof, wherein $R_1$ and $R_3$, which may be the same or different, each represents, a lower alkyl group having 1 to 4 carbon atoms, a benzyl group or a phenyl group, in which the aromatic nucleus of the benzyl and phenyl groups may be substituted with a lower alkyl group having 1 to 4 carbon atoms, a lower alkoxy group having 1 to 4 carbon atoms or a di-lower alkylamino group having 1 to 4 carbon atoms in each of the alkyl moieties thereof; $R_2$ and $R_4$, which may be the same or different, each represents a hydrogen atom, a lower alkyl group having 1 to 4 carbon atoms, a benzyl group or a phenyl group, in which the aromatic nucleus of the benzyl and phenyl groups may be substituted with a halogen atom or a di-lower alkylamino group having 1 to 4 carbon atoms in each of the alkyl moieties thereof; $R_5$ represents a hydrogen atom, a lower alkyl group having 1 to 4 carbon atoms, a lower alkoxy group having 1 to 4 carbon atoms, a halogen atom, a di-lower alkylamino group having 1 to 4 carbon atoms in each of the alkyl moieties thereof, a dibenzylamino group, an N-lower alkyl-N-benzylamino group having 1 to 4 carbon atoms in the lower alkyl moiety thereof or an N-lower alkyl-N-phenylamino group having 1 to 4 carbon atoms in the lower alkyl thereof, in which the aromatic nucleus of the benzylamino and phenylamino groups may be substituted with a halogen atom, a lower alkyl group having 1 to 4 carbon atoms, or a lower alkoxy group having 1 to 4 carbon atoms; and X represents a lower alkyl group having 1 to 4 carbon atoms, a lower alkenyl group having 2 to 4 carbon atoms, a cyclohexyl group, an aralkyl group having 1 to 4 carbon atoms in the alkyl moiety thereof or an aryl group, wherein the aromatic nucleus of the aralkyl and aryl groups may be substituted with a lower alkyl group having 1 to 4 carbon atoms, a lower alkoxy group having 1 to 4 carbon atoms, a di-lower alkylamino group having 1 to 4 carbon atoms in each of the alkyl moieties thereof, a halogen atom, a nitro group, and when the aralkyl group is a benzyl group, the aromatic nucleus thereof may also be substituted with an N-lower alkyl-N-phenyl amino group having 1 to 4 carbon atoms in the N-lower alkyl moiety thereof.

It has also been found that a pressure-sensitive copying member capable of forming an optionally desired color by using the above novel color former in combination with a known color former or color formers can be obtained.

DETAILED DESCRIPTION OF THE INVENTION

In the above general formulas (Ia) and (Ib), suitable examples of lower alkyl groups having 1 to 4 carbon atoms include methyl, ethyl, propyl, iso-propyl, n-butyl, sec-butyl and tert-butyl groups. Suitable examples of lower alkoxy groups having 1 to 4 carbon atoms include methoxy, ethoxy, propoxy, iso-propoxy, n-butoxy, sec-butoxy and tert-butoxy. Suitable examples of di-lower alkylamino groups having 1 to 4 carbon atoms in each of the alkyl moieties thereof include N,N-dimethylamino, N-methyl-N-ethylamino, N-ethyl-N-iso-propylamino, N-methyl-N-butylamino, etc., groups. Typical examples of halogen atoms which can be employed are chlorine, bromine, and iodine atoms. Suitable examples of N-lower alkyl-N-benzyl groups include N-methyl-N-benzyl, N-ethyl-N-benzyl, N-propyl-N-benzyl, etc., groups. Suitable examples of N-lower alkyl-N-phenyl groups include N-methyl-N-phenyl, N-ethyl-N-phenyl, N-propyl-N-phenyl, etc., groups. In addition, suitable examples of N-lower alkyl-N-benzylamino groups include N-methyl-N-benzylamino, N-ethyl-N-benzylamino, N-propyl-N-benzylamino groups, and suitable examples of N-lower alkyl-N-phenylamino groups include N-methyl-N- phenylamino, N-ethyl-N-phenylamino, N-n-propyl-N-phenylamino groups, etc. Typical examples of alkenyl groups having 2 to 4 carbon atoms include ethenyl, propenyl, 1-butenyl and 2-butenyl groups. Suitable examples of aralkyl groups include benzyl, phenethyl, phenylpropyl, etc., groups. Suitable examples of aryl groups include phenyl and naphthyl groups.

The novel color former represented by the formula (Ia), (Ib) or a mixture thereof which can be used in the present invention is a substantially colorless or slightly colored powder which is stable in the atmosphere but undergoes changes in color to purple to green upon heating. The powder is soluble in or miscible with natural or synthetic high molecular weight compounds such as animal, vegetable and mineral waxes, ethyl cellulose, polyvinyl acetate, rosin-modified alkyd resins and the like, and is also soluble in a wide variety of organic liquids such as methanol, ethanol, ethyl Cellosolve, chloroform, benzene, toluene, chlorobenzenes, alkylnaphthalenes, ethylene glycol, diethylphthalate, naphthylalkyl alcohol, benzyltoluene, dibenzyltoluene, dibenzylbenzene, trioctylphosphate and the like. A solution of the powder in an organic liquid enumerated above is adsorbed onto a color developer, for example, an active clay substace such as acid clay, attapulgite, zeolite, bentonite and the like; a solid organic acid such as succinic acid, maleic acid, tannic acid, benzoic acid and the like; and an acidic polymer such as carboxypolyethylene, a phenol-aldehyde copolymer, a styrene/maleic anhydride copolymer having free acid groups and the like thereby developing a purple to green color. The color thus developed has a high color density and has excellent light-fastness, water-resistance and anti-sublimation properties.

Pressure-sensitive copying members such as pressure-sensitive copying papers using as a color former the novel benzoxaxine derivative of the formula (Ia), the novel benzodioxane derivative of the formula (Ib) or a mixture thereof are colorless or slightly colored before color reaction, but when in contact with the color developer, immediately a purple to green color with high color density is formed. The thus formed color is excellent in light-fastness, water-resistance and anti-sublimation property.

Further, pressure-sensitive copying papers using the color former of the present invention in combination with a known color former or formers immediately form an optional color when brought into contact with the color developer. The thus formed color undergoes little change in hue with the lapse of time after color formation.

The benzoxazine derivative of the formula (Ia) and the benzodioxane derivative of the formula (Ib) which can be used for the pressure-sensitive copying papers of the present invention can be prepared as follows:

A triphenylmethane derivative of the formula (II)

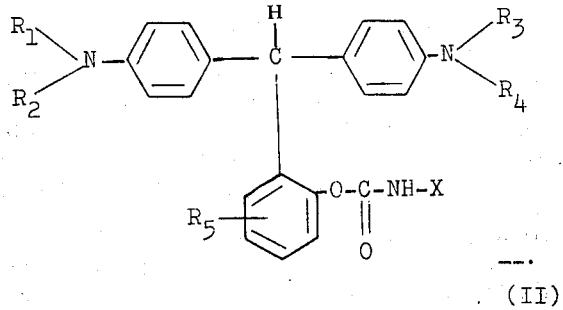

(II)

wherein $R_1$, $R_2$, $R_3$, $R_4$, $R_5$ and X are as defined above is dispersed or dissolved in water or a volatile inert organic solvent such as methanol, ethanol, benzene, toluene, chlorobenzenes and the like, preferably dissolved in the volatile inert organic solvent described above, and the resulting dispersion or solution is oxidized using an inorganic oxidizing agent such as hydrogen peroxide, manganese dioxide, lead peroxide, hypochlorous acid and the like or an organic oxidizing agent such as chloranil, p-benzoquinone, anthraquinone and the like, with an organic oxidizing agent being preferred. A suitable amount of the oxidizing agent can range from about 0.7 to 2, preferably 0.9 to 1.5 mol, per mole of the triphenylmethane derivative of the formula (II). Subsequently, the reaction mixture is treated with an aqueous solution of an inorganic basic compound such as sodium hydroxide, sodium carbonate or sodium bicarbonate and the like or an organic basic compound such as triethylamine, triethanolamine and the like, with an inorganic compound being preferred, e.g., simply rendered alkaline, to obtain a compound of the formula (Ia), (Ib) or a mixture thereof.

The triphenylmethane derivatives having the formula (II) which can be used for the preparation of the color former of the present invention can be prepared using the processes described below.

1. 1 mole of a 4-substituted-amino-4'-substituted-aminobenzhydrol and 1 to 1.5 moles of a substituted phenol are reacted in a volatile solvent such as methanol, ethanol, benzene or toluene or water and the like in the presence of a condensing agent such as hydrochloric acid, sulfuric acid, boric acid, zinc chloride, aluminum chloride, and the like at a temperature of from about 20° to 110°C for a period of from 2 to 10 hours to obtain a crystalline (4-substituted-aminophenyl)-(4-substituted-aminophenyl)-(2-hydroxy-substituted-phenyl)methane.

1 Mole of the thus obtained compound and 0.9 to 1.2 moles of an isocyanate compound, e.g., having the formula X-NCO wherein X is as herein defined, are then reacted in a volatile inert organic solvent such as benzene, toluene, chlorobenzenes and the like, and if desired, in the presence of a small amount of a volatile tertiary amine, e.g., a tertiary amine having 1 to 4 carbon atoms in each of the alkyl moieties, such as triethylamine, as a catalyst at a temperature of from 20° to 110°C for 1 to 5 hours to obtain a crystalline (4-substituted-aminophenyl)-(4-substituted-aminophenyl)-(2-N-substituted-carbamoyloxy)-substituted-phenyl)-methane.

2. 1 Mole of a 4-substituted-amino-4'-substituted-aminobenzhydrol and 1 to 1.5 moles of an N-substituted-carbamoyloxy-substituted-benzene are reacted in the same solvent as described in (1) above in the presence of the same condensing agent as described in (1) above at 20° to 100°C for 2 to 10 hours to obtain a crystalline (4-substituted-aminophenyl)-(4-substituted-aminophenyl)-(2-N-substituted-carbamoyloxy-substituted-phenyl)-methane. If desired, the product may be recrystallized.

3. 2 Moles of an N-substituted-aniline and 0.9 to 1.1 moles of a substituted-salicylaldehyde are reacted in the presence of urea and 1 to 1.5 moles of zinc chloride at a temperature of 50° to 120°C for about 5 to 15 hours to obtain a crystalline (4-substituted-aminophenyl)-(4-substituted-aminophenyl)-(2-hydroxy-substituted-phenyl)-methane. If desired, the product may be recrystallized.

1 Mole of the thus obtained product and 0.9 to 1.2 moles of an isocyanate compound (e.g., as described in (1) above) are then reacted in the same manner as described in (1) above to obtain a crystalline (4-substituted-aminophenyl)-(4-substituted-aminophenyl)-(2-N-substituted-carbamoyloxy-substituted-phenyl)-methane. If desired, the product may be recrystallized.

4. 2 Moles of a substituted-aniline and 0.9 to 1.1 moles of a 2-N-substituted-carbamoyloxy-substituted-benzaldehyde are reacted in the same manner as described in (3) above to obtain a crystalline (4-substituted-aminophenyl)-(4-substituted-aminophenyl)-(2-N-substituted-carbamoyloxy-substituted-phenyl)-methane. If desired, the product may be recrystallized.

5. 1 Mole of a 4-substituted-amino-4'-substituted-amino-substituted-benzophenone and 0.9 to 1.3 moles of a substituted-phenol are reacted in phosphorus oxychloride at a temperature of 30° to 90°C for 1 to 5 hours to obtain a (4-substituted-aminophenyl-(4-substituted-aminophenyl)-(2-hydroxy-substituted-phenyl)-methane.

1 Mole of the thus obtained compound and 0.9 to 1.2 moles of an isocyanate compound (e.g., as described in (1) above) are then reacted in the same manner as described in (1) above to obtain a crystalline (4-substituted-aminophenyl)-(4-substituted-aminophenyl)-(2-N-substituted-carbamoyloxy-substituted-phenyl)-methane. If desired, the product may be recrystallized.

6. 1 Mole of a 4-substituted-amino-4'-substituted-amino-benzophenone and 0.9 to 1.1 moles of 2-N-substituted-carbamoyloxy-substituted-benzaldehyde are reacted in the same manner as described in (5) to obtain a crystalline (4-substituted-aminophenyl)-(4-substituted-aminophenyl)-(2-N-substituted-carbamoyloxy-substituted-phenyl)-methane. If desired, the product may be recrystallized.

7. 1 Mole of a 4'-substituted-amino-2-hydroxy-substituted-benzophenone and 0.9 to 1.5 moles of a substituted-aniline are reacted in the presence of phosphorus oxychloride at a temperature of 20° to 100°C for 2 to 8 hours to obtain a crystalline (4-substituted-aminophenyl)-(4-substituted-aminophenyl)-(2-hydroxy-substituted-phenyl)-methane. If desired, the product may be recrystallized.

1 Mole of the thus obtained compound and 0.9 to 1 mole of an isocyanate compound (e.g., as described in (1) above) are then reacted in the same manner as described in (1) above to obtain a crystalline (4-substituted-aminophenyl)-(4-substituted-aminophenyl)-(2-N-substituted-carbamoyloxy-substituted-phenyl)-methane. If desired, the product may be recrystallized.

8. 1 Mole of a 4'-substituted-amino-2-N-substituted-carbamoyloxy-substituted-benzophenone and 0.9 to 1.5 moles of a substituted-aniline are reacted in the presence of phosphorus oxychloride in the same manner as described in (7) above to obtain a crystalline (4-substituted-aminophenyl)-(4-substituted-aminophenyl)-(2-N-substituted-carbamoyloxy-substituted-phenyl)-methane. If desired, the product may be recrystallized.

Of these processes for preparing the triphenylmethane derivatives, the process as described in (1) above is preferred. For example, bis(4-dimethylaminophenyl)-[2-N-phenyl)carbamoyloxy-4-diethylaminophenyl]-methane can be prepared as follows:

To an aqueous solution of 20 ml of concentrated hydrochloric acid, 100 ml of water and 17 ml of methanol were added 20 g of 4,4'-bis(dimethylamino)-benzhydrol followed by 13.5 g of 3-dimethylaminophenol. The resulting solution was allowed to react at 70° to 80°C for 5 hours while stirring. After completion of the reaction, the reaction mixture was cooled to room temperature (about 20°–30°C) and adjusted to a pH of 10 to 11 with a dilute aqueous solution of sodium hydroxide. The precipitate thus formed was filtered, washed with water and dried to obtain 30.6 g of a blue solid. The solid was recrystallized from a benzene-ethanol solution (2:1 by volume) to obtain 24.7 g of bis(4-dimethylamino-phenyl)-(2-hydroxy-4-diethylaminophenyl)-methane as pale blue crystals having a melting point of 94° to 95°C.

12 g of the above obtained bis(4-dimethylaminophenyl)-(2-hydroxy-4-diethylaminophenyl)-methane was added to 50 ml of toluene, and 10 drops of triethylamine were then added thereto. 3.8 g of phenyl isocyanate was added to the solution, and the resulting mixture was allowed to react at a temperature of 40° to 45°C for 1 hour. After completion of the reaction, the mixture was cooled to 5° to 10°C. The precipitate formed was filtered and recrystallized from toluene to obtain 18.7 g of bis(4-dimethylaminophenyl)-[2-(N-phenyl)carbamoyloxy-4-diethylaminophenyl]-methane as substantially colorless crystals having a melting point of 145° to 146°C.

A preferred embodiment for the preparation of the novel benzoxazine derivative of the formula (Ia) and/or the novel benzodioxane derivative of the formula (Ib) is given below:

1 Mole of a triphenylmethane derivative having the formula (II) is dissolved in 0.5 to 2.5 liters of benzene, toluene or chlorobenzenes. 0.4 to 0.7 moles of chloranil or p-benzoquinone is added to the resulting solution, and the mixture is stirred at a temperature of 15° to 90°C for 0.5 to 7 hours. After the reaction mixture is cooled to room temperature, a dilute aqueous solution of sodium hydroxide is added thereto to adjust the pH of the mixture to 10 to 12. The benzene, toluene or chlorobenzene layer is separated and washed with water followed by distillation to remove benzene, toluene or chlorobenzene whereby a substantially colorless or slightly colored color former represented by the formula (Ia), (Ib) or a mixture thereof can be obtained as crystals.

The proportion of the color former of the formula (Ia) to the color former of the formula (Ib) varies depending upon the chemical structure of the color former obtained, the process employed for the preparation thereof and the like, but regardless of the proportion, any color former according to the present invention can be used.

If desired, the color former thus obtained can be repeatedly recrystallized using a solvent, such as methanol, ethanol, benzene, toluene or a mixture thereof, to obtain the desired compound having either of the formula (Ia) or (Ib) in high purity.

Representative compounds having the formula (Ia), (Ib) or a mixture thereof which can be used for the pressure-sensitive copying papers of the present invention are those prepared from the following triphenylmethane derivatives having the formula (II) as shown in Table I below.

Table I

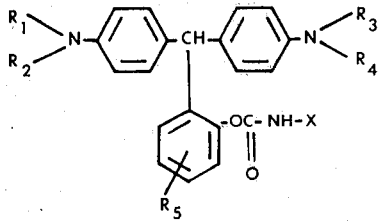

| $R_1$ | $R_2$ | $R_3$ | $R_4$ | X | $R_5$ Substituent | Substituent Position |
|---|---|---|---|---|---|---|
| —CH₃ | —CH₃ | —CH₃ | —CH₃ | —CH₃ | H | |
| " | " | " | " | —CH₂=CHCH₂ | H | |
| " | " | " | " | —CH₂—⌬ | H | |
| " | " | " | " | —CH₂—(naphthyl) | H | |
| " | " | " | " | —CH₂—(naphthyl) | H | |
| " | " | " | " | —⌬—Cl | H | |
| " | " | " | " | (methylnaphthyl) | H | |
| " | " | " | " | —C₄H₉—(n) | H | |
| " | " | " | " | —C₄H₉—(i) | H | |
| " | " | " | " | —⌬(H) | H | |
| " | " | " | " | —CH₂CH₂—⌬ | H | |
| " | " | " | " | —CH₂CH₂—⌬—Cl | H | |
| " | " | " | " | —CH₂—⌬—N(CH₃)₂ | H | |
| —CH₂—⌬ | " | —CH₂—⌬ | " | —C₂H₅ | H | |
| ⌬—CH₃ | " | ⌬—CH₃ | " | —CH₃ | H | |
| ⌬—OCH₃ | " | ⌬—OCH₃ | " | —C₂H₅ | H | |
| ⌬—N(CH₃)₂ | " | ⌬—N(CH₃)₂ | " | ⌬ | H | |
| —CH₃ | " | —CH₃ | " | —CH₃ | —N(C₂H₅)₂ | (4-position) |
| " | " | " | " | —C₄H₉(n) | —N(C₂H₅)₂ | (4-position) |
| " | " | " | " | —⌬(H) | " | " |
| " | " | " | " | —CH₂—⌬ | " | " |

Table I-continued

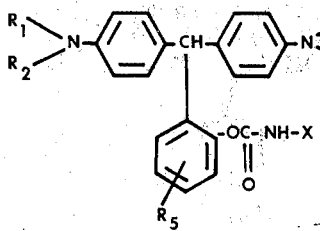

| R₁ | R₂ | R₃ | R₄ | X | R₅ Substituent | Substituent Position |
|---|---|---|---|---|---|---|
| '' | '' | '' | '' |  | '' | '' |
| '' | '' | '' | '' |  | '' | '' |
| —C₂H₅ | —C₂H₅ | —C₂H₅ | —C₂H₅ |  | —CH₃<br>—CH₃ | (4-position)<br>(5-position) |
| —CH₃ | —CH₃ | —CH₃ | —CH₃ |  | —N(CH₃)₂ | (4-position) |
| '' | '' | '' | '' |  | —N(C₂H₅)₂ | (5-position) |
| '' | '' | '' | '' |  | '' | '' |
| '' | '' | '' | '' | —CH₃ |  | '' |
| '' | '' | '' | '' |  |  | (5 position) |
| —C₂H₅ | —C₂H₅ | —C₂H₅ | —C₂H₅ |  | —N(CH₃)₂ | '' |
| —CH₃ | —CH₃ | —CH₃ | —CH₃ | —C₂H₅ |  | '' |
| —C₄H₉(n) | '' | —C₄H₉(n) | '' | '' |  | '' |
| —CH₃ | '' | —CH₃ | '' | '' | —OCH₃ | '' |
| '' | '' | '' | '' |  | Cl<br>Cl | (4-position)<br>(5-position) |
| '' | '' | '' | '' |  | —OC₂H₅ | (4-position) |
| '' | —H | '' | —H |  | —N(CH₃)₂ | '' |
| —CH₂ |  | —CH₂ |  | '' | '' | '' |
| —CH₂ |  | —CH₂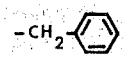 | 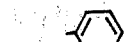 | —CH₃ | —N(CH₃)₂ | (4 position) |

Table I-continued

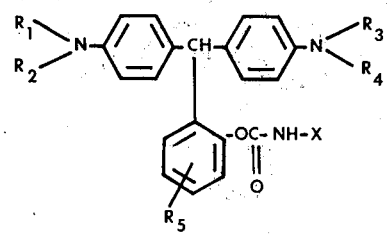

| R₁ | R₂ | R₃ | R₄ | X | R₅ Substituent | Substituent Position |
|---|---|---|---|---|---|---|
| —C₆H₅ | —CH₃ | —C₆H₅ | —CH₃ | —H | —OCH₃ | " |
| —CH₃ | —C₆H₄Cl | —CH₃ | —C₆H₄Cl | —CH₃ | —N(CH₃)₂ | " |
| —C₆H₅ | —CH₃ | —C₂H₅ | —CH₃ | —C₆H₅ | —N(CH₃)(C₂H₅) | " |
| " | " | —CH₂C₆H₅ | " | —C₂H₅ | —N(CH₃)₂ | " |
| —CH₂C₆H₅ | —CH₂C₆H₅ | " | —CH₂C₆H₅ | —CH₃ | " | " |
| —CH₃ | —CH₃ | —CH₃ | —CH₃ | —C₂H₅ | —N(CH₃)(C₆H₃(CH₃)) | " |
| " | " | " | " | " | —N(CH₃)(C₆H₄Cl) | " |
| " | —C₂H₅ | " | —C₂H₅ | —CH₃ | —N(CH₃)—CH₂—C₆H₄Cl | (4 position) |
| " | —CH₂C₆H₄Cl | " | —CH₂C₆H₄Cl | —H | —OCH₃ | " |
| " | —CH₂C₆H₄N(CH₃)₂ | " | —CH₂C₆H₄N(CH₃)₂ | —CH₃ | —N(CH₃)₂ | " |

The process for preparing the color former used in the present invention, i.e., benzoxazine derivatives and/or benzodioxane derivatives, will now be illustrated by the following Preparation Examples. In these Preparation Examples and Examples hereinafter given, all parts, percentages, ratios and the like are by weight unless otherwise indicated.

PREPARATION EXAMPLE 1

Preparation of 4,4-bis(4'-Dimethylaminophenyl)-3-methyl-7-diethylamino-3H-1,3-benzoxazine-2-one and/or 4,4-bis(4'-Dimethylaminophenyl)-2-methylimino-7-diethylamino-1,3-benzodioxane 4.0 g of bis(4-dimethylaminophenyl)-[2-(N-methyl)-carbamoyloxy-4-diethylaminophenyl]-methane was dissolved in 80 ml of benzene, and 2.0 g of chloranil was added to the solution. The resulting mixture was allowed to react at a temperature of 40° to 45°C for 7 hours. After completion of the reaction, the reaction mixture was cooled to room temperature. The benzene layer was removed and washed successively with a dilute aqueous solution of sodium hydroxide and water followed by treatment with active carbon. The benzene was distilled off to obtain 3.0 g of a mixture of 4,4-bis(-4'-dimethylaminophenyl)-3-methyl-7-diethylamino-3H-1,3-benzoxazine-2-one and 4,4-bis(4'-dimethylaminophenyl)-2-methylimino-7-diethylamino-1,3-benzodioxane as substantially colorless crystals having a melting point of 220° to 223°C (Color Former No. 1). When the thus obtained crystals were allowed to stand in the atmosphere for a long period of time or when a solution of the crystals in dibenzyltoluene was exposed to direct sunlight for a long period of time, the crystals did not decompose or develop a color and no decrease in color developing ability was observed. A toluene solution of the crystals was adsorbed on acid clay or a phenol resin, and a pale blue color was developed several minutes later. The thus developed color changed into a intense blue color about 24 hours after the color formation. This intense blue color exhibited an extremely excellent water-resistance, light-fastness and anti-sublimation properties.

The IR spectrum of the crystals showed a strong absorption at 1720 cm$^{-1}$ (>C=O), at 1640 cm$^{-1}$ (>C=N—) and at 1100 cm$^{-1}$

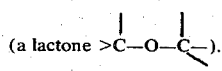
(a lactone >C—O—C—).

2.0 g of the above obtained crystals was repeatedly recrystallized from benzene-petroleum ether (3:1 by volume) to obtain 0.3 g of 4,4-bis(4'-dimethylaminophenyl)-3-methyl-7-diethylamino-3H-1,3-benzoxazine-2-one represented by the formula

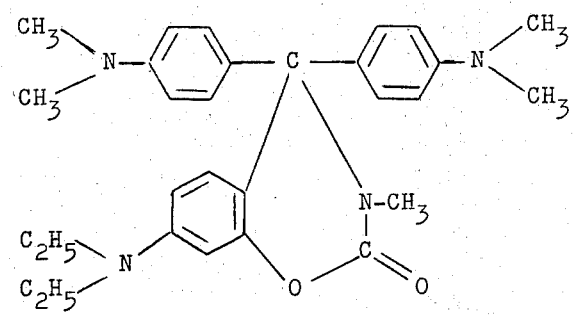

in high purity as substantially colorless crystals having a melting point of 215° to 217°C (Color Former No. 2). The IR spectrum of these crystals showed a strong absorption at 1720 cm$^{-1}$ but no absorption at 1640 cm$^{-1}$ and 1100 cm$^{-1}$. A benzene solution of the thus obtained crystals developed a pale blue color immediately after adsorption on acid clay, which color changed to an intense blue several hours later.

The mother liquor which had been set aside after isolating the above described compound was repeatedly recrystallized from benzene-methanol-petroleum ether (5:2:1 by volume) to obtain 1.1 g of 4,4-bis(4'-dimethylaminophenyl)-2-methylimino-7-diethylamino-1,3-benzodioxane represented by the formula

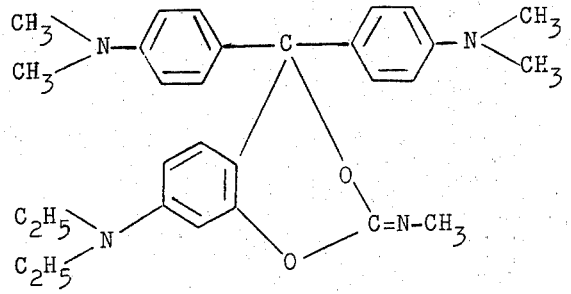

in high purity as substantially colorless crystals having a melting point of 222° to 224°C (Color Former No. 3). The IR spectrum of the crystals showed a strong absorption at 1640 cm$^{-1}$ and 1100 cm$^{-1}$ and a weak adsorption at 1720 cm$^{-1}$. A benzene solution of the crystals was adsorbed on acid clay. Several hours later a pale blue color was observed and 24 hours later the color changed to an intense blue.

PREPARATION EXAMPLE 2

Preparation of
4,4-bis(4'-Dimethylaminophenyl)-3-phenyl-7-diethylamino-3H-1,3-benzoxazine-2-one and/or
4,4-bis(4'-Dimethylaminophenyl)-2-phenylimino-7-diethylamino-1,3-benzodioxane 4.0 g of bis(4-dimethylaminophenyl)-[2-(N-phenyl)-carbamoyloxy-4-diethylaminophenyl]-methane was dissolved in 80 ml of benzene, and 1.8 g of chloranil was added to the solution. The resulting mixture was allowed to react at a temperature of 40° to 50°C for 7 hours, and the reaction product was worked up in the same manner as described in Example 1 to obtain 1.7 g of a mixture of 4,4-bis(4'-dimethylaminophenyl)-3-phenyl-7-diethylamino-3H-1,3-benzoxazine-2-one represented by the formula

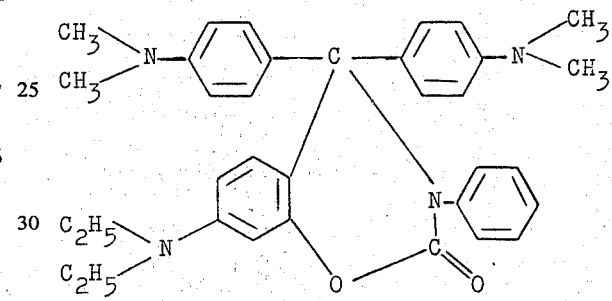

and 4,4-bis(4'-dimethylaminophenyl)-2-phenylimino-7-diethylamino-1,3-benzodioxane represented by the formula

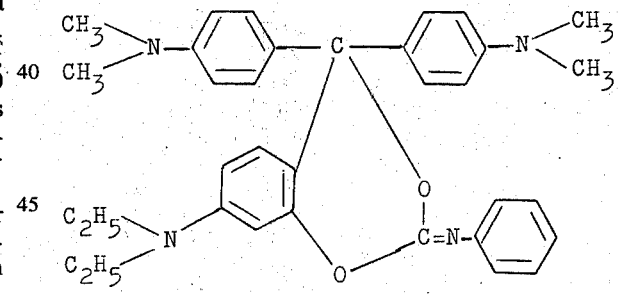

as a substantially colorless powder having a melting point of 204° to 206°C (Color Former No. 4). A benzene solution of the thus obtained powder developed an intense blue color several hours after adsorption on acid clay. The color thus developed had an extremely excellent water-resistance, light-fastness and anti-sublimation properties.

1.0 g of the above obtained powder was repeatedly recrystallized from benzene-petroleum ether (3:1 by volume) in the same manner as described in Example 1 to obtain 0.9 g of 4,4-bis(4'-dimethylaminophenyl)-3-phenyl-7-diethylamino-3H-1,3-benzoxazine-2-one in high purity as substantially colorless crystals having a melting point of 206° to 207°C (Color Former No. 5). The IR spectrum of this product showed a strong absorption at 1720 cm$^{-1}$ but almost no absorption at 1640 cm$^{-1}$ and 1100 cm$^{-1}$. A toluene solution of the above crystals developed a heavy blue color about 2 hours after adsorption on acid clay.

PREPARATION EXAMPLES 3 TO 5

The triphenylmethane derivative of the formula (II) indicated in Table II below was reacted in the same manner as described in Preparation Example 1 to obtain the color former of the formula (Ia) or (Ib) as shown in Table II below. The physical properties of the thus obtained color former and the color developed with the color former are also shown in Table II below.

Table II

| Color Former No. | Triphenylmethane Derivative Represented by the Formula (II) (amount used) | Color Former Represented by the Formula (Ia) or Ib) | | |
|---|---|---|---|---|
| | | Yield (g) | Melting Point (°C) | Crystal Appearance |
| 6 | bis(4-Dimethylaminophenyl)-[2-(N-methyl)carbamoyloxyphenyl]-methane (3.0 g) | 2.1 | 187–191 | 4,4-bis(4'-Dimethylaminophenyl-3-methyl-3H-1,3-benzoxazine-2-one and 4,4-bis(4'-Dimethylaminophenyl)-2-methylimino-1,3-benzodioxane Pale greenish white |
| 7 | bis(4-Dimethylaminophenyl)-[2-(N-benzyl)carbamoyloxyphenyl]-methane (1.0 g) | 0.3 | 230–234 | 4,4-bis(4'-Dimethylaminophenyl-3-benzyl-3H-1,3-benzoxazine-2-one and 4,4-bis(4'-Dimethylaminophenyl)-2-benzylimino-1,3-benzodioxane Pale greenish white |
| 8 | bis(4-Dimethylaminophenyl)-[2-(N-4'-chlorophenyl)-carbamoyloxy-4-diethylaminophenyl]-methane (2.0 g) | 1.6 | 219–223 | 4,4-bis(4'-Dimethylaminophenyl)-3-(4'-chloro)-phenyl-7-diethylamino-3H-1,3-benzoxazine-2-one and 4,4-bis(4'-Dimethylaminophenyl)-2-(4'-chloro)-phenylimino-7-diethylamino-1,3-benzodioxane Pale bluish white |
| 9 | bis(4-Dimethylaminophenyl)-[2-(N-4'-methylphenyl-carbamoyloxy-4-diethylaminophenyl]-methane (2.0 g) | 1.8 | 184–188 | 4,4-bis(4'-Dimethylaminophenyl)-3-(4'-methyl)phenyl-7-diethylamino-3H-1,3-benzoxazine-2-one and 4,4-bis(4'-Dimethylaminophenyl)-2-(4'-methyl)phenyl-imino-7-diethylamino-1,3-benzodioxane Pale bluish white |
| 10 | bis(4-Dimethylaminophenyl)-[2-(N-1'-naphthyl)carbamoyloxy-4-diethylaminophenyl]-methane (2.0 g) | 1.6 | 199–201 | 4,4-bis(4'-Dimethylaminophenyl)-3-(1'-naphthyl)-7-diethylamine-3H-1,3-benzoxazine-2-one and 4,4-bis-(4'Dimethylaminophenyl)-2-(1'-naphthyl)imino-7-diethylamino-1,3-benzodioxane Pale bluish white |
| 11 | bis(4-Dimethylaminophenyl)-[2-(N-4'-methoxyphenyl-carbamoyloxy-4-dibenzylaminophenyl]-methane (1.0 g) | 0.4 | 171–176 | 4,4-bis(4'-Dimethylaminophenyl)-3-(4'-methoxy)-phenyl-7-dibenzylamino-3H-1,3-benzoxazine-2-one and 4,4-bis(4'-Dimethylaminophenyl)-2-(4'-methoxy)phenylimino-7-dibenzylamino-1,3-benzodioxane Pale bluish white |
| 12 | bis(4-Dimethylaminophenyl)-[2-(N-ethyl)carbamoyloxy-4-methoxyphenyl]-methane (2.0 g) | 1.2 | 169–173 | 4,4-bis(4'-Dimethylaminophenyl)-3-ethyl-7-methoxy-3H-1,3-benzoxazine-2-one and 4,4-bis(4'-Dimethylaminophenyl)-2-ethylimino-7-methoxy-1,3-benzodioxane Pale bluish white |
| 13 | bis(4-Dimethylaminophenyl)-[2-(N-n-butyl)carbamoyloxy-4-diethylaminophenyl]-methane (2.0 g) | 1.3 | 197–199 | 4,4-bis(4'-Dimethylaminophenyl)-3-n-butyl-7-diethyl-amino-3H-1,3-benzoxazine-2-one and 4,4-bis(4'-Dimethylaminophenyl)-2-n-nbutylimino-7-diethylamino-1,3-benzodioxane Pale bluish white |
| 14 | bis(4-Dimethylaminophenyl)-[2-(N-cyclohexyl)carbamoyloxy-4-diethylaminophenyl]-methane (2.0 g) | 1.4 | 173–178 | 4,4-bis(4'-Dimethylaminophenyl)-3-cyclohexyl-7-diethylamino-3H-1,3-benzoxazine-2-one and 4,4-bis(4'-Dimethylaminophenyl)-2-cyclohexylimino-7-diethylamino-1,3-benzodioxane Pale bluish white |
| 15 | bis(4-Dimethylaminophenyl-[2-(N-benzyl)carbamoyloxy-4-diethylaminophenyl]-methane (2.0 g) | 1.5 | 201–205 | 4,4-bis(4'-Dimethylaminophenyl)-3-benzyl-7-diethyl-amino-3H-1,3-benzoxazine-2-one and 4,4-bis(4'-Dimethylaminophenyl)-2-benzylimino-7-diethylamino-1,3-benzodioxane Pale bluish white |
| 16 | bis(4-Dimethylaminophenyl)-[2-(N-allyl)carbamoyloxyphenyl]-methane (3.0 g) | 1.2 | | 4,4-bis(4'-Dimethylaminophenyl)-3-allyl-3H-1,3-benzoxazine-2-one and 4,4-bis(4'-Dimethylamino phenyl)-2-allylimino-1,3-benzodioxane Pale greenish white |
| 17 | bis(4-Dimethylaminophenyl)-[2-(N-i-butyl)carbamoyloxyphenyl]-methane (3.0 g) | 1.8 | | 4,4-bis(4'-Dimethylaminophenyl)-3-i-butyl-3H-1,3-benzoxazine-2-one and 4,4-bis(4'-Dimethyl-aminophenyl)-2-i-butylimino-1,3-benzodioxane Pale bluish white |
| 18 | bis(4-Dimethylaminophenyl)-[2-(N-cyclohexyl)carbamoyl-oxyphenyl]-methane (2.0 g) | 0.9 | | 4,4-bis(4'-Dimethylaminophenyl)-3-cyclohexyl-3H-1,3-benzoxazine-2-one and 4,4-bis(4'-Dimethylamino-phenyl-2-cyclohexylimino-1,3-benzodioxane White |
| 19 | bis(4-Dimethylaminophenyl)-[2-(N-phenethyl)carbamoyloxyphenyl]-methane (2.0 g) | 1.0 | | 4,4-bis(4'-Dimethylaminophenyl)-3-phenethyl-3H-1,3-benzexazine-2-one and 4,4-bis(4'-Dimethylamino-phenyl)-2-phenethylimino-1,3-benzodioxane Pale greenish white |
| 20 | bis(4-Dimethylaminophenyl)-[2-N- 4'-(N'-methyl-N'-phenyl)aminobenzyl carbamoyloxyphenyl]-methane (3.0 g) | 1.1 | | 4,4-bis(4'-Dimethylaminophenyl)-3-[4'-(N-methyl-N-benzyl)aminophenyl]-3H-1,3-benzoxazine-2-one and 4,4-bis(4'-Dimethylaminophenyl)-2-[4'(N-methyl-N-benzyl)aminophenylimino]-1,3-benzodioxane Pale bluish greenish white |
| 21 | bis(4-Dimethylaminophenyl)-[2-N-1'-naphthylmethyl)-carbamoyloxyphenyl]-methane (2.0 g) | 0.5 | | 4,4-bis(4'-Dimethylaminophenyl)-3-(1'-naphthyl-methyl)-3H-1,3-benzoxazine-2-one and 4,4-bis(4'-Dimethylaminophenyl)-2-(1'-naphthylmethyl)imino-1,3-benzodioxane Pale greenish white |
| 22 | bis[4-(N-Methyl-N-benzyl)-aminophenyl]-[2-N-ethyl)-carbamoyloxyphenyl]-methane (2.0 g) | 0.4 | | 4,4-bis[4'-(N-Methyl-N-benzyl)aminophenyl]-3-ethyl-3H-1,3-benzoxazine-2-one and 4,4-bis[4'-(N-Methyl-N-benzyl)aminophenyl]-2-ethylimino-1,3-benzodioxane Pale purple |
| 23 | bis(4-Methylaminophenyl)-[2-(N-phenyl)carbamoyloxy-4- | | | 4,4-bis(4'-Methylaminophenyl)-3-phenyl-7-dimethyl-amino-3H-1,3-benzoxazine-2-one and 4,4-bis(4'- |

Table II-continued

| Color Former No. | Triphenylmethane Derivative Represented by the Formula (II) (amount used) | Color Former Represented by the Formula (Ia) or (Ib) | Yield (g) | Melting Point (°C) | Crystal Appearance |
|---|---|---|---|---|---|
| | dimethylaminophenyl]-methane (2.0 g) | Methylaminophenyl)-2-phenylimino-7-dimethylamino-1,3-benzodioxane | 0.5 | | Pale purplish white |
| 24 | bis(4-Dimethylaminophenyl)-[2-(N-3'-dimethylaminophenyl)-carbamoyloxy-4-dimethylaminophenyl]-methane (2.0 g) | 4,4-bis(4'-Dimethylaminophenyl)-3-(3'-dimethylaminophenyl)-7-dimethylamino-3H-1,3-benzoxazine-2-one and 4,4-bis(4'-Dimethylaminophenyl)-2-(3'-dimethylamino)phenylimino-7-dimethylamino-1,3-benzodioxane | 0.3 | | Pale bluish white |
| 25 | bis(4-Diethylaminophenyl)-[2-(N-3'-nitrophenyl)carbamoyloxy-4,5-dimethylphenyl]-methane (2.0 g) | 4,4-bis(4'-Diethylaminophenyl)-3-(3'-nitrophenyl)-7,8-dimethyl-3H-1,3-benzoxazine-2-one and 4,4-bis(4'-Diethylaminophenyl)-2-(3'-nitrophenyl)imino-7,8-dimethyl-1,3-benzodioxane | 1.5 | | Pale bluish white |
| 26 | bis(4-Dimethylaminophenyl)-[2-(N-methyl)carbamoyloxy-4-(N-methyl-N-benzyl)aminophenyl]-methane (3.0 g) | 4,4-bis(4'-Dimethylaminophenyl)-3-methyl-7-(N-methyl-N-benzyl)amino-3H-1,3-benzoxazine-2-one and 4,4-bis(4-Dimethylaminophenyl)-2-methylimino-7-(N-methyl-N-benzyl)amino-1,3-benzodioxane | 1.2 | | Pale purplish bluish white |
| 27 | bis(4-Dimethylaminophenyl)-[2-(N-4'-benzylphenyl)-carbamoyloxy-4,5-dichlorophenyl]-methane (3.0 g) | 4,4-bis(4'-Dimethylaminophenyl)-3-(4'-benzylphenyl)-6,7-dichloro-3H-1,3-benzoxazine-2-one and 4,4-bis-(4'-Dimethylaminophenyl)-2-(4'-benzylphenyl)imino-6,7-dichloro-1,3-benzodioxane | 1.5 | | Pale greenish white |
| 28 | bis(4-Dimethylaminophenyl)-[2-N-4'-chloro-1-'-naphthyl)-carbamoyloxy-4-ethoxyphenyl]-methane (3.0 g) | 4,4-bis(4'-Diethylaminophenyl)-3-(4'-chloro-1'-naphthyl)-7-ethoxy-3H-1,3-benzoxazine-2-one and 4,4-bis(4'-Dimethylaminophenyl)-2-(4'-chloro-1'-naphthyl)imino-7-ethoxy-1,3-benzodioxane | 0.8 | | White |
| 29 | bis(4-Dibenzylaminophenyl)-[2-(N-methyl)carbamoyloxy-4-dimethylaminophenyl]-methane (3.0 g.) | 4,4-bis(4'-Dibenzylaminophenyl)-3-methyl-7-dimethylamino-3H-1,3-benzoxazine-2-one and 4,4-bis(4'-Dibenzylaminophenyl)-2-methylimino-7-dimethylamino-1,3-benzodioxane | 0.7 | | Pale bluish white |
| 30 | bis[4-(N-Benzyl-N-phenyl)-aminophenyl]-[2-N-phenyl)-carbamoyloxy-4-dimethylaminophenyl]-methane (2.0 g) | 4,4-bis[4'-N-Benzyl-N-phenyl)aminophenyl]-3-phenyl-7-dimethylamino-3H-1,3-benzodazine-2-one and 4,4-bis[4'-(N-Benzyl-N-phenyl)aminophenyl]-2-phenylimino-7-dimethylamino-1,3-benzodioxane | 0.4 | | Pale bluish green |
| 31 | bis[4-(N-4'-methylphenyl-N-methyl)aminophenyl]-[2-(N-methyl)carbamoyloxyphenyl]-methane (3.0 g) | bis[4-(N-4'-methylphenyl-phenyl]-3-methyl-3H-1,3-benzoxazine-2-one and 4,4-bis[4'-(N-4''-Methylphenyl-N-methyl)aminophenyl]-2-methylimino-1,3-benzodioxane | 2.1 | | Pale bluish green |

Processes of producing pressure-sensitive copying members using the benzoxazine derivative of the formula (Ia), the benzodioxane derivative of the formula (Ib) or a mixture thereof, as a color former are well known in the art and include the method in which complex coacervation is utilized to produce microcapsules as disclosed in U.S. Pat. Nos. 2,800,457 and 2,800,458. The color former is generally used in an amount of from about 0.5 to 5% by weight based on the weight of the organic solvent. Suitable organic solvents are solvents such as ethylene glycol, chlorobenzenes, dibenzylbenzene, dibenzyltoluene, diethylphthalate, trioctylphosphate, alkylnaphthalenes, and naphthylalkyl alcohols, etc. Suitable examples of pressure-sensitive copying members applicable to this invention are described in detail in U.S. Pat. No. 3,427,180.

Pressure-sensitive copying members using as a color former at least one of the benzoxazine derivative of the formula (Ia), the benzodioxane derivative of the formula (Ib) and a mixture thereof generally comprise a combination of a sheet having the microencapsulated color former coated thereon and a sheet having a color developer coated thereon or comprise a sheet having both the microcapsules containing the color former and the color developer coated on the same surface thereof.

A pressure-sensitive copying paper using the color former of the formula (Ia) and/or (Ib) will now be illustrated in greater detail by reference to the following Examples. The invention is not to be construed as being limited to these Examples.

EXAMPLE 1

2.0 g of Color Former No. 1 was dissolved in 100 g of 4-naphthyl-n-butyl alcohol and 20 g of gum arabic and 160 g of water were added thereto at a temperature of 50°C to emulsify. 20 g of acid-treated gelatin and 160 g of water were added to the resulting emulsion, and under stirring, acetic acid was added thereto to adjust the pH to 5. 500 g of water was then added thereto to allow coacervation to proceed thereby forming a thick, liquid film of gelatin-gum arabic around oil droplets of the 4-naphthyl-n-butyl alcohol having the color former dissolved therein. After adjusting the pH to 4.4, 4 g of a 37% formaldehyde aqueous solution was added thereto to harden the above-described liquid film. Then, the system was cooled to 10°C and, after adjusting the pH to 9 with dilute aqueous sodium hydroxide, allowed to stand for 5 to 6 hours to complete the encapsulation.

The resulting microcapsule-containing liquid was applied to a sheet of paper by a coating method such as roll-coating and air knife-coating, etc., and dried to obtain a colorless coated paper (upper sheet paper). When the resulting coated paper was allowed to stand in the atmosphere for a long period of time or exposed to direct sun-light for a long period of time, no decomposition or color development was observed. Thus, the resulting coated paper had excellent stability, light-fastness and anti-sublimation properties and no decrease in color developing capability was observed.

The thus obtained upper sheet paper was intimately superposed on a lower sheet paper having coated thereon an active clay substance and/or an acidic organic polymer as a color developer and a localized pressure was applied to the assembly by handwriting. Immediately after the application of the pressure, almost no color formation was observed on the lower sheet paper at the pressed area, but several minutes after the application of the pressure a pale blue color was developed, which color changed into an intense blue color 24 hours after the color formation. Almost no discoloration or fading of the thus developed intense blue color was observed even when the paper was exposed directly to sun-light for a long period of time and also excellent water-resistance and anti-sublimation properties were exhibited by the paper.

EXAMPLE 2

The same procedures as described in Example 1 were repeated except that 2.0 g of Color Former No. 2 was employed to obtain a colorless upper sheet paper. When this upper sheet paper was allowed to stand in the atmosphere for a long period of time or exposed directly to sun-light for a long period of time, no decomposition or color formation was observed and the upper sheet paper posessed stability and light-fastness without any decrease in color developing capability.

When this upper sheet paper was intimately superposed on a lower sheet paper having coated thereon an active clay substance and/or an acidic organic polymer as a color developer and a localized pressure was applied thereby by handwriting, a pale blue color was immediately developed on the lower sheet paper at the pressed area, which color changed into an intense blue several hours later. Almost no discoloration or fading of the thus developed intense blue color was observed even when the paper was directly exposed to sun-light for a long period of time. The developed color also had excellent water-resistance and anti-sublimation properties.

EXAMPLE 3

The same procedures as described in Example 1 were repeated except that 2.0 g of Color Former No. 3 was used to obtain a colorless upper sheet paper. The resulting paper was intimately superposed on a lower sheet paper having coated thereon an active clay substance an/or an acidic organic polymer as a color developer. When a localized pressure was applied to the assembly by handwriting, a pale blue color was formed on the lower sheet paper at the pressed area several hours after the pressure-application, which color changed into an intense blue about 24 hours later. The thus formed color had excellent water-resistance and anti-sublimation properties and almost no discoloration or fading was observed even when the paper was directly exposed to sun-light for a long period of time.

EXAMPLE 4

The procedures as described in Example 1 were repeated except that 2.0 g of each of Color Former Nos. 4 and 5 was employed to obtain a colorless upper sheet paper. The resulting sheet paper was intimately superposed on a lower sheet paper having coated thereon an active clay substance and/or an acidic organic polymer as a color developer. When a localized pressure was applied to the assembly by handwriting, an intense blue color was developed on the lower sheet paper at the pressed area. The thus developed intense blue color exhibited a sufficiently stable light-fastness with the lapse of time for practical use, and also had excellent water-resistance and anti-sublimation properties.

EXAMPLE 5

The procedures as described in Example 1 were repeated using 2.0 g of each of Color Former Nos. 6 to 30. When each of the resulting papers was intimately superposed on a lower sheet paper having coated thereon an acid clay substance and/or an acidic organic polymer as a color developer, and a localized pressure was applied to the assembly by handwriting, an intense color image was developed on the lower sheet paper at the pressed area. The hues developed on the lower sheets are shown in Table III below.

Table III

| Color Former | Hue | Color Former | Hue |
|---|---|---|---|
| No.6 | intense bluish green | No.7 | intense bluish green |
| No.8 | intense blue | No.9 | intense blue |
| No.10 | intense blue | No.11 | intense purplish blue |
| No.12 | intense greenish blue | No.13 | intense blue |
| No.14 | intense blue | No.15 | intense blue |
| No.16 | intense bluish green | No.17 | intense bluish green |
| No.18 | intense bluish green | No.19 | intense bluish green |
| No.20 | intense bluish green | No.21 | intense bluish green |
| No.22 | intense purplish blue | No.23 | intense bluish purple |
| No.24 | intense blue | No.25 | intense greenish blue |
| No.26 | intense purplish blue | No.27 | intense greenish blue |
| No.28 | intense purple | No.29 | intense purple |
| No.30 | intense greenish blue | | |

EXAMPLE 6

The procedures as described in Example 1 were repeated except 1.0 g of Color Former No. 1, 0.5 g of Crystal Violet Lactone, 0.3 g of 3,6-dimethoxyfluoran and 1.5 g of 2,7-bis-diethylaminofluoran were used as the color former to prepare an upper sheet paper. When the resulting upper sheet paper was superposed on a lower sheet paper having coated thereon an active clay substance as a color developer and a localized pressure was applied to the assembly by handwriting, a black color was immediately developed on the lower sheet paper. Substantially no change in the hue of or fading of the developed black color was observed.

While the present invention has been described in detail and with reference to specific embodiments thereof, it will be apparent to one skilled in the art that various changes and modifications can be made therein without departing from the spirit and scope thereof.

What is claimed is:

1. A pressure-sensitive copying material comprising a support having thereon a microencapsulated color former capable of forming a color on contact with an electron-donating color developer, the color former comprising at least one of a benzoxazine derivative represented by the formula (Ia)

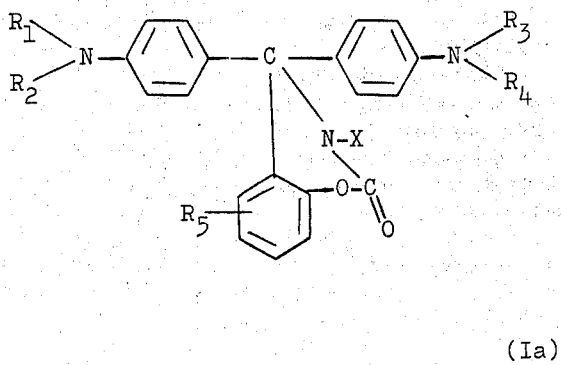

(Ia)

, a benzodioxane derivative represented by the formula (Ib)

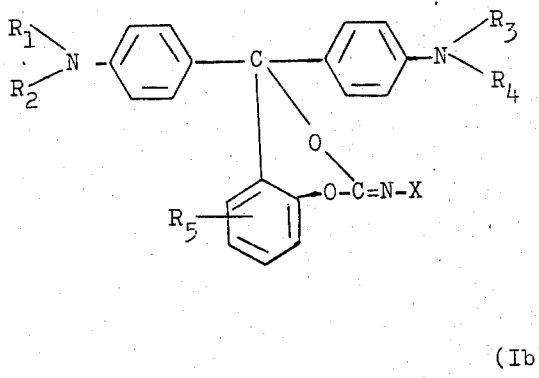

(Ib)

or a mixture thereof; wherein $R_1$ and $R_3$, which may be the same or different, each represents a lower alkyl group having 1 to 4 carbon atoms, a benzyl group or a phenyl group, in which the aromatic nucleus of the benzyl and phenyl groups may be substituted with a lower alkyl group having 1 to 4 carbon atoms, a lower alkoxy group having 1 to 4 carbon atoms or a di-lower alkylamino group having 1 to 4 carbon atoms in each of the alkyl moieties thereof; $R_2$ and $R_4$, which may be the same or different, each represents a hydrogen atom, a lower alkyl group having 1 to 4 carbon atoms, a benzyl group or a phenyl group, in which the aromatic nucleus of said benzyl and phenyl groups may be substituted with a halogen atom or a di-lower alkylamino group having 1 to 4 carbon atoms in each of the alkyl moieties thereof; $R_5$ represents a hydrogen atom, a lower alkyl group having 1 to 4 carbon atoms, a lower alkoxy group having 1 to 4 carbon atoms, a halogen atom, a di-lower alkylamino group having 1 to 4 carbon atoms in each of the alkyl moieties thereof, a dibenzylamino group, an N-lower alkyl-N-benzylamino group having 1 to 4 carbon atoms in the lower alkyl moiety thereof, an N-lower alkyl-N-benzylamino group having 1 to 4 carbon atoms in the lower moiety thereof, in which the aromatic nucleus of the benzyl and phenyl groups may be substituted with a halogen atom, a lower alkyl group having 1 to 4 carbon atoms, or a lower alkoxy group having 1 to 4 carbon atoms; and X represents a lower alkyl group having 1 to 4 carbon atoms, a lower alkyl group having 2 to 4 carbon atoms, a cyclohexyl group, an aralkyl group having 1 to 4 carbon atoms in the alkyl moiety thereof or an aryl group, in which the aromatic nucleus of said aralkyl and aryl groups may be substituted with a lower alkyl group having 1 to 4 carbon atoms, a lower alkoxy group having 1 to 4 carbon atoms, a di-lower alkylamino group having 1 to 4 carbon atoms in each of the alkyl moieties thereof, a halogen atom, a nitro group, and when the aralkyl group is a benzyl group, the aromatic nucleus thereof may also be substituted with an N-lower alkyl-N-phenyl amino group having 1 to 4 carbon atoms in the N-lower alkyl moiety thereof.

2. The pressure-sensitive copying paper as claimed in claim 1, wherein said mixture is selected from the group consisting of
 a. a mixture of 4,4-bis(4'-dimethylaminophenyl)-3-methyl-7-diethylamino-3H-1,3-benzoxazine-2-one and 4,4-bis(4'-dimethylaminophenyl)-2-methylimino-7-diethylamino-1,3-benzdioxane,
 b. a mixture of 4,4-bis(4'-dimethylaminophenyl)-3-phenyl-7-diethylamino-3H-1,3-benzoxazine-2-one and 4,4-bis(4'-dimethylaminophenyl)-2-phenylimino-7-diethylamino-1,3-benzodioxane,
 c. a mixture of 4,4-bis(4'-dimethylaminophenyl)-3-(1'-naphthyl)-7-diethylamino-3H-1,3-benzoxazine-2-one and 4,4-bis(4'-dimethylaminophenyl)-2-(1'-naphthyl)imino-7-diethylamino-1,3-benzodioxane,
 d. a mixture of 4,4-bis(4'-dimethylaminophenyl)-3-cyclohexyl-7-diethylamino-3H-1,3-benzoxazine-2-one and 4,4-bis(4'-dimethylaminophenyl)-2-cyclohexylimino-7-diethylamino-1,3-benzodioxane, and
 e. a mixture of 4,4-bis(4'-dimethylaminophenyl)-3-benzyl-7-diethylamino-3H-1,3-benzoxazine-2-one and 4,4-bis(4'-dimethylaminophenyl)-2-benzylimino-7-diethylamino-1,3-benzodioxane.

3. The pressure-sensitive copying paper as claimed in claim 1, wherein said mixture is selected from the group consisting of
 a. a mixture of 4,4-bis(4'-dimethylaminophenyl)-3-methyl-3H-1,3-benzoxazine-2-one and 4,4-bis(4'-dimethylaminophenyl)-2-methylimino-1,3-benzodioxane,
 b. a mixture of 4,4-bis(4'-dimethylaminophenyl)-3-benzyl-3H-1,3-benzoxazine-2-one and 4,4-bis(4'-dimethylaminophenyl)-2-benzylimino-1,3-benzodioxane,
 c. a mixture of 4,4-bis(4'-dimethylaminophenyl)-3-allyl-3H-1,3-benzoxazine-2-one and 4,4-bis(4'- dimethylaminophenyl)-2-allylimino-1,3-benzodioxane,
d. a mixture of 4,4-bis(4'-dimethylaminophenyl)-3-cyclohexyl-3H-benzoxazine-2-one and 4,4-bis(4'-dimethylaminophenyl)-2-cyclohexylimino-1,3-benzodioxane, and
e. a mixture of 4,4-bis(4'-dimethylaminophenyl)-3-[4'-(N-methyl-N-benzyl)aminophenyl]-3H-1,3-benzoxazine-2-one and 4,4-bis(4'-dimethylaminophenyl)-2-[4'-(N-methyl-N-benzyl)aminophenylimino]-1,3-benzodioxane.

4. The pressure-sensitive copying paper as claimed in claim 1, wherein said mixture is selected from the group consisting of
a. a mixture of 4,4-bis(4'-dimethylaminophenyl)-3-methyl-7-(N-methyl-N-benzyl)amino-3H-1,3-benzoxazine-2-one and 4,4-bis(4'-dimethylaminophenyl)-2-methylimino-7-(N-methyl-N-benzyl)imino-1,3-benzodioxane,
b. a mixture of 4,4-bis(4'-dimethylaminophenyl)-3-(4'-benzylphenyl)-6,7-dichloro-3H-1,3-benzoxazine-2-one and 4,4-bis(4'-dimethylaminophenyl)-2-(4'-benzylphenyl)imino-6,7-dichloro-1,3-benzodioxane and
c. a mixture of 4,4-bis(4'-diethylaminophenyl)-3-(3'-nitrophenyl)-7,8-dimethyl-3H-1,3-benzoxazine-2-one and 4,4-bis(4'-diethylaminophenyl)-3-(3'-nitrophenyl)-7,8-dimethyl-3H-1,3-benzodioxane.

5. The pressure-sensitive copying material of claim 1, wherein said support includes at least one color developer thereon.

6. The pressure-sensitive copying material of claim 5, wherein said color developer and said color former microcapsules are on the same surface of said support.

7. The pressure-sensitive copying material of claim 5, wherein said color developer and said color former microcapsules are on opposite surfaces of said support.

8. A pressure-sensitive copying assembly comprising the pressure-sensitive copying material of claim 1, and a color developer member comprising a support having thereon a color developer material.

* * * * *